(12) United States Patent
Kanjolia et al.

(10) Patent No.: US 10,155,783 B2
(45) Date of Patent: Dec. 18, 2018

(54) MANGANESE COMPLEXES AND USE THEREOF FOR PREPARING THIN FILMS

(71) Applicant: Sigma-Aldrich Co., LLC., St. Louis, MO (US)

(72) Inventors: Ravi Kanjolia, North Andover, MA (US); Shaun Garratt, Wirral (GB)

(73) Assignee: Merck Patent GmbH, Darmstadt (DE)

( * ) Notice: Subject to any disclaimer, the term of this patent is extended or adjusted under 35 U.S.C. 154(b) by 207 days.

(21) Appl. No.: 14/909,360

(22) PCT Filed: May 28, 2014

(86) PCT No.: PCT/US2014/039717
§ 371 (c)(1),
(2) Date: Feb. 1, 2016

(87) PCT Pub. No.: WO2014/193915
PCT Pub. Date: Dec. 4, 2014

(65) Prior Publication Data
US 2016/0185807 A1 Jun. 30, 2016

Related U.S. Application Data

(60) Provisional application No. 61/827,993, filed on May 28, 2013.

(51) Int. Cl.
| | | |
|---|---|---|
| C23C 16/00 | (2006.01) | |
| C07F 13/00 | (2006.01) | |
| B01J 31/00 | (2006.01) | |
| C07F 17/00 | (2006.01) | |
| C23C 16/18 | (2006.01) | |
| C23C 16/455 | (2006.01) | |

(52) U.S. Cl.
CPC ............ *C07F 13/005* (2013.01); *B01J 31/00* (2013.01); *C07F 17/00* (2013.01); *C23C 16/18* (2013.01); *C23C 16/45553* (2013.01)

(58) Field of Classification Search
CPC ............................. C07F 13/005; C07F 17/00
See application file for complete search history.

(56) References Cited

U.S. PATENT DOCUMENTS

| | | |
|---|---|---|
| 4,581,249 A | 4/1986 | Kamiya |
| 6,072,081 A | 6/2000 | Itagaki et al. |
| 6,353,084 B1 | 3/2002 | Warzelhan et al. |
| 2006/0040822 A1* | 2/2006 | Shveima ............ C08F 10/00 502/103 |
| 2006/0100123 A1 | 5/2006 | Schlingloff et al. |
| 2008/0076931 A1 | 3/2008 | Itagaki et al. |

(Continued)

FOREIGN PATENT DOCUMENTS

| | | |
|---|---|---|
| WO | WO-2015/065823 A1 | 5/2015 |
| WO | WO-2015/138390 A1 | 9/2015 |

OTHER PUBLICATIONS

George, S.M., et al. (1996), "Surface Chemistry for Atomic Layer Growth", *J. Phys. Chem.* 100: 13121-13131.

(Continued)

*Primary Examiner* — Kelly M Gambetta
(74) *Attorney, Agent, or Firm* — Harness, Dickey & Pierce, P.L.C.

(57) ABSTRACT

Manganese complexes, methods of making the same, and use thereof in thin film deposition, such as CVD and ALD are provided herein.

19 Claims, 2 Drawing Sheets

(56) References Cited

U.S. PATENT DOCUMENTS

| | | |
|---|---|---|
| 2008/0076941 A1 | 3/2008 | Itagaki et al. |
| 2009/0247492 A1 | 10/2009 | Maurel et al. |
| 2010/0200991 A1 | 8/2010 | Akolkar et al. |
| 2011/0060165 A1 | 3/2011 | Cameron et al. |
| 2012/0053306 A1 | 3/2012 | Ito et al. |
| 2012/0077989 A1 | 3/2012 | Noel et al. |
| 2012/0142934 A1* | 6/2012 | Cheng .................. C07B 37/04 546/343 |
| 2012/0178621 A1 | 7/2012 | Elliott et al. |
| 2013/0041170 A1 | 2/2013 | Odedra et al. |

OTHER PUBLICATIONS

International Preliminary Report on Patentability dated Dec. 10, 2015 issued in PCT Patent Application No. PCT/US2014/039717.
International Search Report and Written Opinion dated Sep. 30, 2014 issued in PCT Patent Application No. PCT/US2014/039717.
Potter, R., et. al. (2005), "Deposition of $HfO_2$ $Gd_2O_3$ and $PrO_x$ by Liquid Injection ALD Techniques", *Chemical Vapor Deposition*: 11(3): 159-169.

\* cited by examiner

MANGANESE COMPLEXES AND USE THEREOF FOR PREPARING THIN FILMS

CROSS-REFERENCE TO RELATED APPLICATIONS

This patent application is a U.S. national stage filing under 35 U.S.C. § 371 of International Application No. PCT/US2014/039717, which has an international filing date of 28 May 2014 and which claims the benefit of U.S. Provisional Patent Application Ser. No. 61/827,993 filed on 28 May 2013. The entire disclosure of each of the above applications is incorporated herein by reference.

FIELD OF THE INVENTION

The present invention relates to manganese (Mn) complexes, methods of making such complexes, and methods of preparing thin films by chemical vapor deposition (CVD) or atomic layer deposition (ALD) using such complexes.

BACKGROUND OF THE INVENTION

Various metal-based precursors are used to form thin metal films and a variety of deposition techniques have been employed. These include reactive sputtering, ion-assisted deposition, sol-gel deposition, CVD (also known as metalorganic CVD or MOCVD), and ALD (also known as atomic layer epitaxy. The CVD and ALD processes are being increasingly used as they have the advantages of good compositional control, high film uniformity, good control of doping and, significantly, they give excellent conformal step coverage on highly non-planar microelectronics device geometries.

CVD is a chemical process whereby precursors are used to form a thin film on a substrate. In a typical CVD process, the precursors are passed over a substrate (e.g., a wafer) in a low pressure or ambient pressure reaction chamber. The precursors react and/or decompose on the substrate surface creating a thin film of deposited material. Volatile by-products are removed by gas flow through the reaction chamber. The deposited film thickness can be difficult to control because it depends on coordination of many parameters such as temperature, pressure, gas flow volumes and uniformity, chemical depletion effects, and time.

ALD is also a method for the deposition of thin films. It is a self-limiting sequential, unique film growth technique based on surface reactions that can provide precise thickness control deposit conformal thin films of materials provided by precursors onto substrates varying compositions. In ALD, the precursors are separated during the reaction. The first precursor is passed over the substrate producing a monolayer on the substrate. Any excess unreacted precursor is pumped out of the reaction chamber. A second precursor is then passed over the substrate and reacts with the first precursor, forming a second monolayer of film over the first-formed monolayer of film on the substrate surface. This cycle is repeated to create a film of desired thickness. ALD film growth is self-limiting and based on surface reactions, creating uniform depositions that can be controlled at the nanometer-thickness scale.

Dielectric thin films have a variety of important applications, such as nanotechnology and fabrication of semiconductor devices. Examples of such applications include high-refractive index optical coatings, corrosion-protection coatings, photocatalytic self-cleaning glass coatings, biocompatible coatings, dielectric capacitor layers and gate dielectric insulating films in field-effect transistors (FETs), capacitor electrodes, gate electrodes, adhesive diffusion barriers and integrated circuits. Dielectric thin films are also used in microelectronics applications, such as the high-κ dielectric oxide for dynamic random access memory (DRAM) applications and the ferroelectric perovskites used in infrared detectors and non-volatile ferroelectric random access memories (NV-FeRAMs). The continual decrease in the size of microelectronics components has increased the need for the use of such dielectric thin films.

Manganese-containing films have found numerous practical applications in areas such as catalysts, batteries, memory devices, displays, sensors, and nano- and microelectronics. In the case of electronic applications, manganese-containing films can act as barriers to prevent diffusion of copper interconnects into underlying silicon dioxide substrate (e.g., self-forming diffusion barrier layers).

Current manganese precursors for use in CVD and ALD do not provide the required performance to implement new processes for fabrication of next generation devices, such as semiconductors. For example, improved thermal stability, higher volatility, increased vapor pressures, increased deposition rates and a high premittivity and/or increased barrier properties are needed.

SUMMARY OF THE INVENTION

According to one aspect, a manganese complex of Formula I or a solvate thereof is provided:

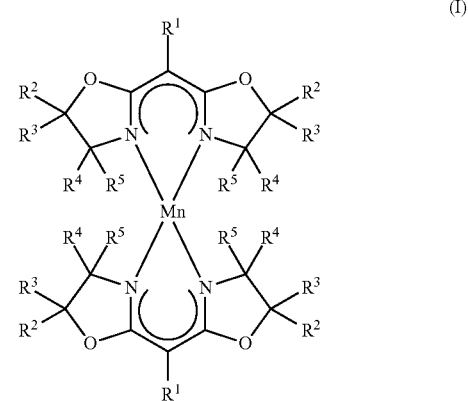

wherein
$R^1$, $R^2$, $R^3$, $R^4$, and $R^5$ are independently selected from the group consisting of hydrogen, alkyl, and trialkylsilyl.

In one embodiment, the manganese complex is selected from the group consisting of

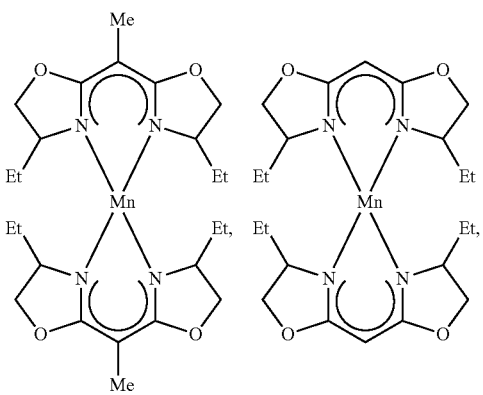

-continued

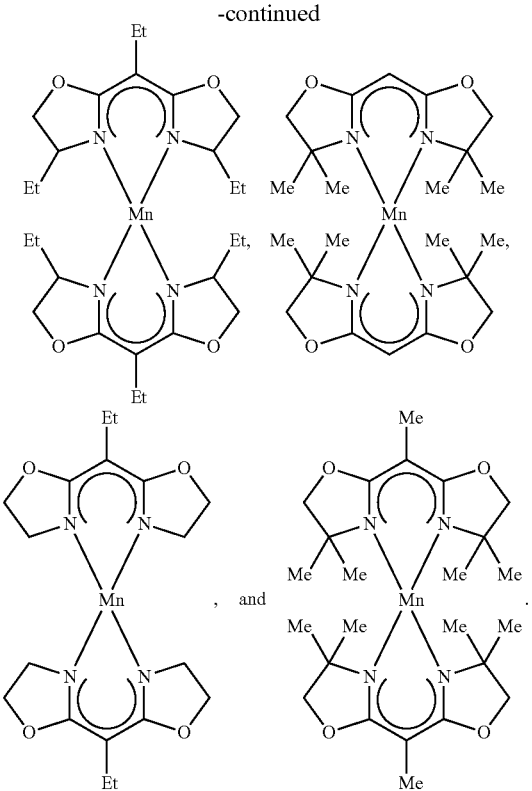

According to another is a method for forming a manganese-containing film by deposition process is provided, the method comprising vaporizing the manganese complex of Formula I ear a solvate thereof.

According to another aspect, a method of making a manganese complex of Formula I, or a solvate thereof, is provided. The method comprises reacting a compound of Formula II:

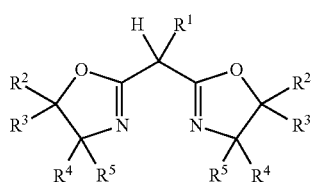

or the conjugate base thereof,
with a manganese salt to provide the manganese complex of Formula I:

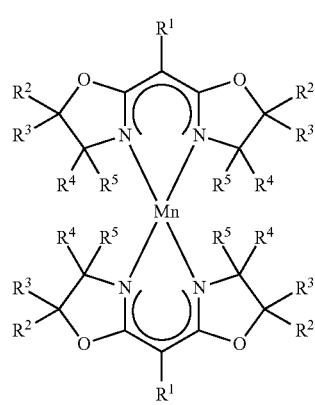

or a solvate thereof, wherein
$R^1$, $R^2$, $R^3$, $R^4$, and $R^5$ are independently selected from the group consisting of hydrogen, alkyl, and trialkylsilyl.

According to another aspect, a manganese complex or a solvate thereof is provided which is prepared by the process of reacting a compound of Formula II:

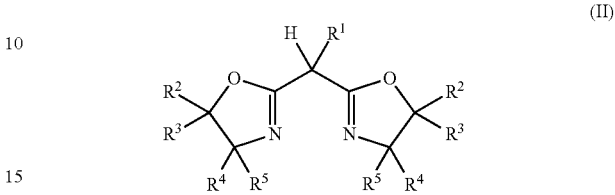

or the conjugate base thereof,
with a manganese salt,
wherein
$R^1$, $R^2$, $R^3$, $R^4$, and $R^5$ are independently selected from the group consisting of hydrogen, alkyl, and trialkylsilyl.

According to another aspect, a method for forming a manganese-containing film by a vapor deposition process is provided, the method comprising vaporizing the manganese complex or a solvate thereof which is prepared by the aforementioned process.

Other embodiments, including particular aspects of the embodiments summarized above, will be evident from the detailed description that follows.

DETAILED DESCRIPTION OF THE INVENTION

Figure 1:
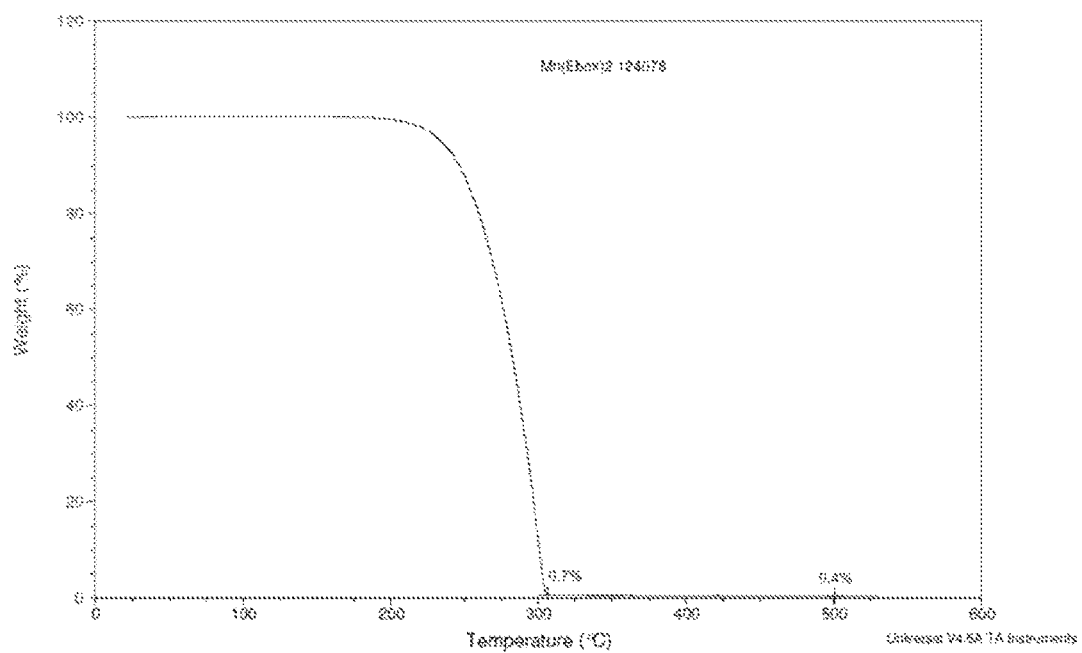
FIG. 1 is a graphical representation of thermal gravimetric analysis (TGA) data demonstrating % weight loss vs. temperature or the mangzinese complex prepared according to Example 2.

In various aspects of the invention, manganese complexes, methods of making such complexes, and methods of using such complexes to form thin manganese-containing films, such as but not limited to, manganese, manganese oxide, manganese nitride, and manganese silicide films, are provided.

The methods of the invention are used to create or grow maganese-containing thin films which display high dielectric constants or which act as barrier films. A dielectric thin film as used herein refers to a thin film having a high permittivity.

As used herein, the term "high-κ dielectric" refers to a material, such as a metal-containing film, with a higher dielectric constant (κ) when compared to silicon dioxide (which has at dielectric constant of about 3.7). Typically, a high-κ dielectric film is used in semiconductor manufacturing processes to replace a silicon dioxide gate dielectric. A high-κ dielectric film may be referred to as having a "high-κ gate property" when the dielectric film is used as a gate material and has at least a higher dielectric constant than silicon dioxide.

As used herein, the term "relative permittivity" is synonymous with dielectric constant (κ).

As used herein, the term "precursor" or "complex" refers to a metal-containing molecule or compound which is deposited on, decomposed on, delivered to, and/or passed over a substrate to form at thin metal film by a vapor deposition process such as CVD or ALD. Unless context clearly indicates otherwise, the complexes disclosed herein are manganese complexes.

As used herein, the term "vapor deposition process" is used to refer to any type of vapor deposition technique such as CVD or ALD. In various embodiments of the invention, CVD may take the form of conventional (i.e., continuous flow) CVD, liquid injection CVD, or photo-assisted CVD. CVD may also take the form of a pulsed technique, i.e., pulsed CVD. In other embodiments, ALD may take the form of conventional (i.e., pulsed injection) ALD, liquid injection ALD, photo-assisted ALD, plasma-assisted ALD, or plasma-enhanced ALD. The term "vapor deposition process" further includes various vapor deposition techniques described in *Chemical Vapour Desposition: Precursors, Processes, and Applications*; Jones, A. C.; Hitchman, M. L., Eds. The Royal Society of Chemistry: Cambridge, 2009; Chapter 1, pp 1-36.

The term "alkyl" (alone or in combination with another term(s)) refers to a saturated hydrocarbon chain of 1 to about 12 carbon atoms in length, such as, but not limited to, methyl, ethyl, propyl, butyl, pentyl, hexyl, heptyl, octyl, decyl, and so forth. The alkyl group may be straight-chain or branched-chain. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl. Further, as used herein. "Me" refers to methyl, "Et" refers to ethyl, "i-Pr" refers to isopropyl, "t-Bu" refers to tert-butyl, and "Np" refers to neopentyl. It should also be noted that $C_2$ is intended to refer to an ethyl group and not geminal dimethyl groups. In some embodiments, alkyl groups are $C_1$-$C_8$-alkyl groups.

The term "solvate" refers to a complex of the invention disclosed herein that further includes a stoichiometric or non-stoichiometric amount of solvent associated with the complex. The solvent may be covalently bound to the complex or otherwise associated with the complex, such as for example, through non-covalent intermolecular forces. In some embodiments, the solvate is an ether solvate where one or more ether molecules is covalently bound to the complex or otherwise associated with the complex.

Therefore, according to a first aspect, a manganese complex or a solvate thereof is provided which is prepared by a process comprising reacting a compound of Formula II:

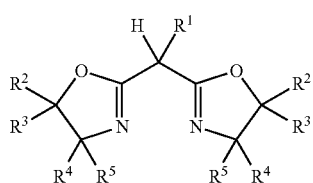

(II)

or the conjugate base thereof,
with a manganese salt,
wherein
$R^1$, $R^2$, $R^3$, $R^4$, and $R^5$ are independently selected from the group consisting of hydrogen, alkyl, and trialkylsilyl.

In one embodiment of the compound of Formula II, $R^1$, $R^2$, $R^3$, $R^4$, and $R^5$ are independently selected from the group consisting of hydrogen, $C_1$-$C_8$-alkyl, and tri($C_1$-$C_8$-alkyl)silyl. In a particular embodiment, $R^1$, $R^2$, $R^3$, $R^4$, and $R^5$ are independently selected from the group consisting of hydrogen, methyl, ethyl, n-propyl, isopropyl, n-butyl, isobutyl, tert-butyl, n-pentyl, neopentyl, n-hexyl, n-heptyl, n-octyl, trimethylsilyl, triethylsilyl, triisopropylsilyl, and tert-butyldimethyisilyl.

In another embodiment of the compound of Formula II, $R^2$ and $R^3$ are each hydrogen such that the compound of Formula II is a compound of Formula IIA:

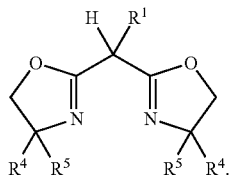

(IIA)

In one embodiment of the compound of Formula IIA, $R^1$, $R^4$, and $R^5$ are independently hydrogen or $C_1$-$C_8$-alkyl.

In another embodiment, the compound of Formula II is selected from the group consisting of

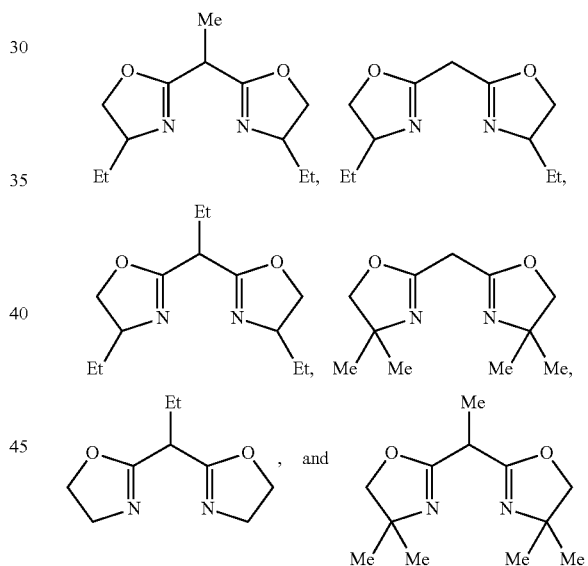

In another embodiment, the manganese complex or solvate thereof prepared by the aforementioned process is paramagnetic.

As will be appreciated by those of skill in the art, the compound of Formula II may be referred to generally as a "bis(oxazoline)" or, when complexed to a metal, as "bis (oxazoline) ligand" (or alternatively, a "BOX ligand"). The preparation of bis(oxazoline) compounds is generally well-known in the art. A bis(oxazoline) may be prepared, for example, by the reaction of an amino alcohol with a malonate ester derivative in the manner described by Dagorne, S., et al., in *Organometailics* 2004, 23, 3053-3061. For instance, various compounds of Formula II may be prepared according to Scheme 1 using commercially available starting materials and reagents.

Scheme 1

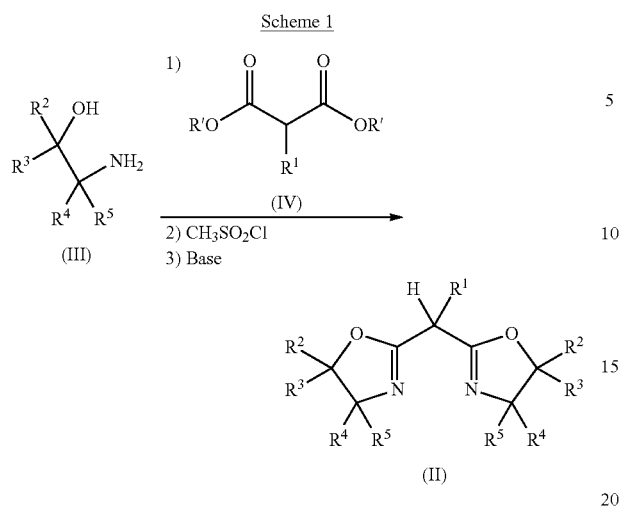

Scheme 2

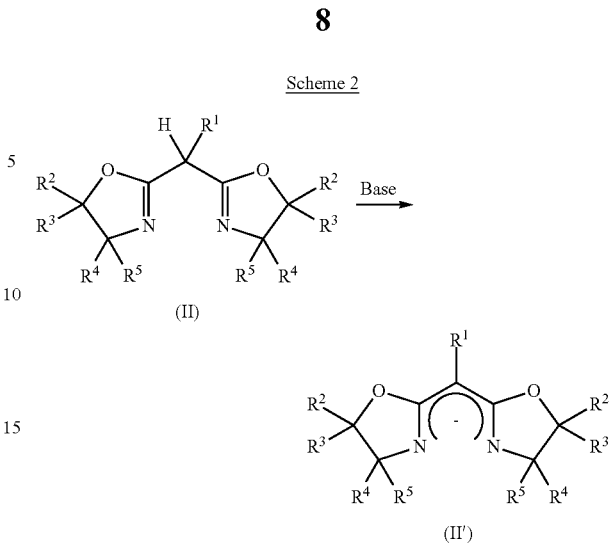

In Scheme 1, the amino alcohol of Formula III is reacted with a malonate ester of Formula IV (R'=alkyl) to provide an intermediate dihydroxy diamide (not shown). Reaction of the dihydroxy diamide with methanesulfonyl chloride provides a bis-mesylated diamide (not shown). Deprotonation with base (e.g., NaOH) provides the compound of Formula II, i.e., a bis(oxamline). In the above reaction scheme, $R^1$, $R^2$, $R^3$, $R^4$, and $R^5$ may be any of those groups previously indicated. Furthermore, any stereoisomers (or mixtures of stereoisomers) of the amino alcohol of Formula III may be used. For example, it is contemplated that an amino alcohol such as alaminol (i.e., $H_2NCH(CH_3)CH_2OH$) may be either a single enantiomer or at mixture of enantiomers (with such mixtures being racemic or non-racemic). Similarly, an amino alcohol with a plurality of stereocenters (e.g., 3-amino-2-butanol) may be used as a single stereoisomer or as at mixture of stereoisomers. In this regard, the use of mixtures of stereoisomers may provide stereoisomeric mixtures of the compound of Formula II, which, upon complexation to manganese, may provide manganese complexes of reduced crystallinity and/or improved volatility in comparison the corresponding manganese complex prepared from stereoisomerically pure compounds of Formula II.

Of course, the preparation of the compound of Formula II as shown in Scheme 1 may be modified in a number of ways which will be apparent to those of skill in the art. For example, other malonate derivatives may be used in place of the compound of Formula IV (e.g., derivatives of Meldrum's acid). Activation reagents other than methanesulfonyl chloride may be used, such as for example, substituted or unsubstituted area sulfonyl halides and pseudohalides (e.g., tosyl chloride), or substituted or unsubstituted alkanesulfonyl halides and pseudohalides (e.g., trifluoromethanesulfonyl chloride).

To prepare the manganese complex, the compound of Formula II, or the conjugate base thereof, is reacted with a manganese salt. Typically, the compound of Formula II or the conjugate base thereof are reacted with the manganese salt in a molar ratio from about 1:1 to about 3:1, and preferably in a molar ratio of about 2:1.

In some embodiments, the compound of the Formula II is treated with a suitable base, such as for example, an alkyllithium reagent (e.g., n-butyllithium) to effect deprotonation as to provide the conjugate base of the compound of Formula II, i.e., the compound of Formula II', as shown in Scheme 2 below.

Thus, where the compound of Formula II' is prepared with alkyllithium reagent, the compound of Formula II' is provided as a lithium salt. The compound of Formula II' is reacted with a manganese salt to provide the manganese complex. Any manganese salt may be used which is capable of complexation to the compound of Formula II'. In some embodiments, the manganese salt is a manganese(II) salt selected from the group consisting of manganese(II) fluoride, manganese(II) chloride, manganese(II) bromide, manganese(II) iodide, manganese(II) nitrate, manganese(II) acetate, manganese(II) sulfate, manganese(II) carbonate, manganese(II) perchlorate, and manganese(II) trifluoromethanesulfonate.

Alternatively, the manganese complex may be directly from prepared from the compound of Formula II if a sufficiently basic manganese salt is used (i.e., the manganese salt is sufficiently basic to deprotonate the compound of Formula II). For example, a manganese(II) bis(trialkylsilyl) amide such as manganese(II) bis(trimethylsilyl)amide (e.g., *Inorg, Chem.* 1998, 27, 1782-1786 to R. A. Andersen et al.) may be reacted directly with the compound of Formula II to provide the manganese complex.

Regardless of how the manganese complex is prepared, it is generally preferred to perform the reaction of the compound of Formula II or the conjugate base thereof with the manganese salt in the presence of one or more solvents. In some embodiments, an ether solvent is used. Examples of suitable ether solvents include, but are not limited to, diethyl ether, tetrahydrofuran (THF), 2-methyltetrahydrofuran, 1,2-dimethoxyethane, 1,4-dioxane, and the like.

The manganese complex may be isolated from the reaction mixture and optionally purified using standard techniques known in the art. For example, the manganese complex may form as a solid precipitate which may be filtered, collected, and purified bye sublimation. Depending the manner of preparation, the identity of solvent(s) used in the complexation reaction, and the method of purification, it is possible that the manganese complex may be isolated as a solvated manganese complex. For instance, where an ether solvent is used for the complexation reaction, manganese complex solvated with ether may be isolated.

The manganese complexes prepared in the above described manner will generally display paramagnetic properties. Such properties make structural characterization of the manganese complexes difficult since techniques such as nuclear magnetic resonance (NMR) spectrometry cannot be successfully employed. Without being bound by any particular theory, it is believed that the manganese complexes thus prepared include two bis(oxazolinyl) ligands and a manganese atom in a 2+ oxidation state, possibly further including solvent molecules which may or may not be coordinated to the manganese atom.

Thus, according to another aspect, the a manganese complex of Formula I, or a solvate thereof is provided:

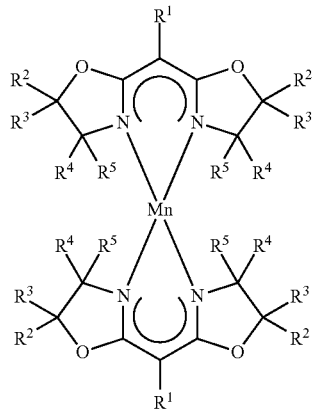

(I)

wherein
R¹, R², R³, R⁴, and R⁵ are independently selected from the group consisting of hydrogen, alkyl, and trialkylsilyl.

In one embodiment, R¹, R², R³, R⁴, and R⁵ are independently selected from the group consisting of hydrogen, $C_1$-$C_8$-alkyl, and tri($C_1$-$C_8$-alkyl)silyl. In a particular embodiment, R¹, R², R³, R⁴, and R⁵ are independently selected from the group consisting of hydrogen, methyl, ethyl, n-propyl, isopropyl, n-butyl, isobutyl, tert-butyl, n-pentyl, neopentyl, n-hexyl, n-heptyl, n-octyl, trimethylsilyl, triethylsilyl, triisopropylsilyl, and tert-butyldimethylsilyl.

In another embodiment, R² and R³ are each hydrogen such that manganese complex of Formula I is a manganese complex of Formula IA:

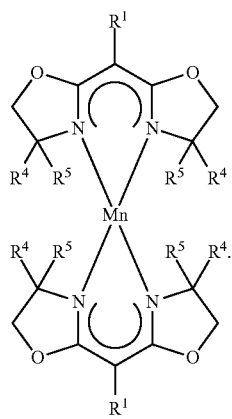

(IA)

In one embodiment of the manganese complex of Formula IA, R¹, R⁴, and R⁵ are independently hydrogen or $C_1$-$C_8$-alkyl.

In another embodiment, the manganese complex is selected from the group consisting of

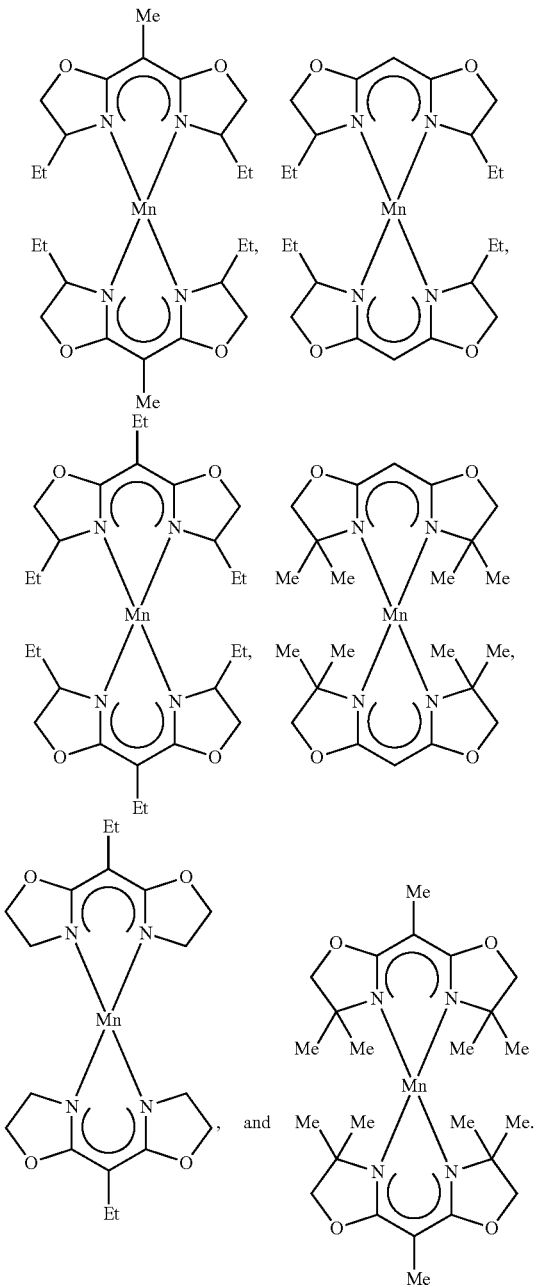

In another embodiment, the manganese complex or solvate thereof is paramagnetic.

According to another aspect, a method of making a manganese complex of Formula I, or a solvate thereof, is provided. The method comprises: reacting a compound of Formula II:

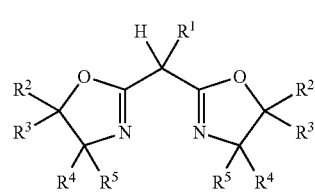

(II)

or the conjugate base thereof, with a manganese salt to provide manganese complex of Formula I:

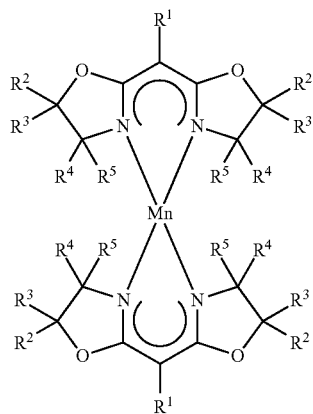

or a solvate thereof,
wherein
$R^1$, $R^2$, $R^3$, $R^4$, and $R^5$ are independently selected from the group consisting of hydrogen, alkyl, and trialkylsilyl.

According to another aspect, a method for forming a manganese-containing film by as vapor deposition process is provided. The method comprises vaporizing: (i) at least one manganese complex or a solvate thereof produced by any of the aforementioned processes (methods) or (II) at least one manganese complex of any of the aforementioned Formulas, including that of Formula I or Formula IA, or as solvate thereof.

The film-forming method may include, for example, (1) vaporizing the at least one manganese complex and (2) delivering the at least one manganese complex to a substrate surface or passing the at least one manganese complex over a substrate (and/or decomposing the at least one manganese complex on the substrate surface).

In a particular embodiment, the manganese complexes may be dissolved in a suitable solvent such as a hydrocarbon or an mine solvent. Appropriate hydrocarbon solvents include, but are not limited to, aliphatic hydrocarbons, such as hexane, heptane and nonane; aromatic hydrocarbons, such as toluene and xylene; and aliphatic and cyclic ethers, such as diglyme, triglyme, and tetraglyme. Examples of appropriate amine solvents include, without limitation, octylamine and N,N-dimethyldodecylamine. For example, the complex may be dissolved in toluene to yield as solution with a concentration from about 0.0.5 M to about 1 M.

In another embodiment, the at least one manganese complex may be delivered "neat" (undiluted by a carrier gas) to a substrate.

In one embodiment, the vapor deposition process is chemical vapor deposition.

In another embodiment, the vapor deposition process is atomic layer deposition.

The ALD and CVD methods of the invention encompass various types of ALD and CVD processes such as, but not limited to, continuous or pulsed injection processes, liquid injection processes, photo-assisted processes, plasma-assisted, and plasma-enhanced processes. For purposes of clarity, the methods of the present invention specifically include direct liquid injection processes. For example, in direct liquid injection CVD ("DLI-CVD"), a solid or liquid complex may be dissolved in a suitable solvent and the solution formed therefrom injected into a vaporization chamber as a means to vaporize the complex. The vaporized complex is then transported/delivered to the substrate. In general, DLI-CVD may be particularly useful in those instances where a complex displays relatively low volatility or is otherwise difficult to vaporize.

In one embodiment, conventional or pulsed CVD is used to form a manganese-containing thin film vaporizing and/or passing the at least one manganese complex over a substrate. For conventional CVD processes see, for example Smith, Donald (1995). *Thin-Film Deposition: Principles and Practice*, McGraw-Hill.

In one embodiment, CVD growth conditions for the manganese complexes disclosed herein include, but are not limited to:
  (1) Substrate temperature: 50-600° C.
  (2) Evaporator temperature (Mn source temperature): 0-200° C.
  (3) Reactor pressure: 0-100 Torr
  (4) Argon or nitrogen carrier gas flow rate: 0-500 sccm
  (5) Oxygen flow rate: 0-500 sccm
  (6) Hydrogen flow rate: 0-500 sccm
  (7) Run time; will vary according to desired film thickness In another embodiment, photo-assisted CVD is used to form a manganese-containing thin film by vaporizing and/or passing at least one manganese complex disclosed herein over a substrate.

In a further embodiment, conventional (i.e., pulsed injection) ALD is used to form a manganese-containing thin film by vaporizing and/or passing at least one manganese complex disclosed herein over a substrate. For conventional ALD processes see, for example, George S. M., et al. *J. Phys. Chem.*, 1996, 100, 13121-13131.

In another embodiment, liquid injection ALD is used to form a manganese-containing thin film by vaporizing and/or passing at least one manganese complex disclosed herein over a substrate, wherein at least one liquid manganese complex is delivered to the reaction chamber by direct liquid injection as opposed to vapor draw by a bubbler. For liquid injection ALD processes see, for example, Potter R. J., et al., *Chem, Vap. Deposition*, 2005, 11(3), 159-169.

Examples of ALD growth conditions for manganese complexes disclosed herein include, but are not limited to:
  (1) Substrate temperature: 0-400° C.
  (2) Evaporator temperature (Mn source temperature): 0-200° C.
  (3) Reactor pressure: 0-100 Torr
  (4) Argon or nitrogen carrier gas now rate: 0-500 sccm
  (5) Reactive gas flow rate: 0-500 sccm
  (6) Pulse sequence (complex/purge/reactive gas/purge): will vary according to chamber size
  (7) Number of cycles: will vary according to desired film thickness In another embodiment, photo-assisted ALD is used to form a manganese-containing thin film by vaporizing and/or passing at least one manganese complex disclosed herein over a substrate. For photo-assisted ALD processes see, for example, U.S. Pat. No. 4,581,249.

In another embodiment, plasma-assisted ALD is used to form a manganese-containing thin film by vaporizing and/or passing at least one manganese complex disclosed herein over a substrate.

Thus, the manganese complexes disclosed herein utilized in these methods may be liquid, solid, or gaseous. Typically, the manganese complexes a are liquids or solids at ambient temperatures with a vapor pressure sufficient to allow for consistent transport of the vapor to the process chamber.

In one embodiment, the manganese complexes disclosed herein are delivered to the substrate in pulses alternating with pulses of an oxygen source, such as a reactive oxygen species. Examples of such oxygen source include, without limitation $H_2O$, $H_2O_2$, $O_2$, ozone, air, i-PrOH, i-BuOH, or $N_2O$.

In one embodiment, a manganese, a manganese nitride, a manganese oxide, or a manganese silicide film can be formed by delivering for deposition at least one manganese complex as disclosed herein, independently or in combination with a co-reactant. In this regard, the co-reactant may be deposited or delivered to or passed over a substrate, independently or in combination with the at least one manganese complex. Examples of such co-reactants include, but are not limited to hydrogen, hydrogen plasma, oxygen, air, water, $H_2O_2$, ammonia, a hydrazine, a borane, a silane, ozone, or combination of any two or more thereof. Examples of suitable boranes include, without limitation, hydridic (i.e., reducing) boranes such as borane, diborane, triborane and the like. Examples of suitable silanes include, without limitation, hydridic silanes such as silane, disilane, trisilane, and the like. Examples of suitable hydrazines include, without limitation, hydrazine ($N_2H_4$) and/or a hydrazine optionally substituted with one or more alkyl groups (i.e., an alkyl-substituted hydrazine) such as methylhydrazine, tert-butylhydrazine, N,N- or N,N'-dimethylhydrazine, and the like.

In a particular embodiment, a co-reactant is used to form as manganese oxide film by delivering for deposition at least one manganese complex as disclosed herein, independently or in combination, with a co-reactant such as, but not limited to, air, $H_2O$, $O_2$, ozone, and/or other oxygen-containing compounds to a reaction chamber. A plurality of such co-reactants may be used.

In another particular embodiment, a co-reactant is used to form a manganese nitride film by delivering for deposition at least one manganese complex as disclosed herein, independently or in combination, with a co-reactant such as, but not limited to, ammonia, a hydrazine, and/or other nitrogen-containing compounds (e.g., an amine) to a reaction chamber. A plurality of such co-reactants may be used.

In another particular embodiment, a co-reactant is used to form a manganese-containing metal film by delivering for deposition at least one manganese complex as disclosed herein, independently or in combination, with a co-reactant such as, but not limited to, $H_2$, a hydrazine a silane, and/or ammonia to a reaction chamber.

In another embodiment, a mixed-metal film can be formed by a vapor deposition process which vaporizes at least one manganese complex as disclosed herein in combination, but not necessarily at the same time, with a co-complex having a metal different from manganese.

A variety of substrates can be used in the methods of the present invention. For example, the manganese complexes as disclosed herein may be delivered or passed over a variety of substrates such as, but not limited to, silicon such as Si(100), silicon oxide, silicon nitride, tantalum, tantalum nitride, copper, ruthenium, titanium nitride, tungsten, and tungsten nitride.

In a particular embodiment, the methods of the invention are utilized for applications such as dynamic random access memory (DRAM) and complementary metal oxide semiconductor (CMOS) for memory and logic applications, on substrates such as silicon chips.

Any of the manganese complexes disclosed herein may be used to prepare thin films of manganese metal, manganese oxides, manganese nitrides, and/or manganese silcides. Such films may find application as oxidation catalysts, anode materials (e.g., SOFC or LIB anodes), conducting layers, sensors, diffusion barriers/coatings, super- and non-superconducting materials/coatings, tribological coatings, and/or, protective coatings. It is understood by one of ordinary skill in the art that the film properties (e.g., conductivity) will depend on as number of factors, such as the metal(s) used for deposition, the presence or absence of co-reactants and/or co-complexes, the thickness of the film created, the parameters and substrate employed during growth and subsequent processing.

Fundamental differences exist between the thermally-driven CVD process and the reactivity-driven ALD process. The requirements for precursor properties to achieve optimum performance vary greatly. In CVD a clean thermal decomposition of the complex to deposit the required species onto the substrate is critical. However, in ALD such a thermal decomposition is to be avoided at all costs. In ALD, the reaction between the input reagents must be rapid at the surface resulting in formation of the target material on the substrate. However, in CVD, any such reaction between species is detrimental due to their gas phase mixing before reaching the substrate, which could lead to particle formation. In general it is accepted that good CVD precursors do not necessarily make good ALD precursors due to the relaxed thermal stability requirement for CVD precursors.

The present invention, thus generally described, will be understood more readily by reference to the following examples, which provided by way of illustration and is not intended to be limiting.

EXAMPLES

The following examples are merely illustrative, and do not limit this disclosure in any way.

Unless otherwise noted, all synthetic manipulations were performed, under an inert atmosphere (e.g., purified nitrogen or argon) using techniques for handling air-sensitive materials commonly known in the an (e.g., Schlenk techniques).

Example 1: Preparation of 1,1-bis(4,4-dimethyl-1,3-oxazolin-2-yl)ethane ($Me_2$-EBOX)

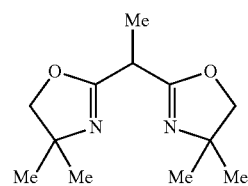

1,1-Bis(4,4-dimethyl-1,3-oxazolin-2-yl)ethane was prepared by adapting as literature procedure from S. Dagorne et al., *Organometellics* 2004, 23, 3053-3061.

Step 1. In a glovebox, sodium hydride (0.1 g, ~0.005 mol) was charged to a 1-L with stirrer bar. Diethyl methylmalonate (43.6 g, 0.250 mol) was added via syringe to the reactor containing sodium hydride with stirring, resulting in the formation of a suspension 2-Amino-2-methyl-1-propanol (44.6 g, 0.500 mol) was then added slowly via a syringe with continued stirring. A collector vessel was attached to a sidearm of the reactor by a glass U-tube. The reaction mixture was then heated to 140° C. for 7 hours, during which time ethanol by-product was observed to transfer to the collector vessel. The reaction mixture was cooled and remaining ethanol was removed under reduced pressure. The resulting solid dihydroxy diamide was collected and dried in vacuo (61.5 g, 95%).

Step 2. The dihydroxy diamide from Step 1 was cooled to 0° C. and triethylamine (126.5 g, 1.25 mol) was added. To this mixture, dichloromethane (600 mL) was added to give a clear solution. Methanesulfonyl chloride (71.6 g, 0.625 mol) was then added drop-wise via a dropping funnel. The solution was allowed to warm to room temperature and then stirred for 2 hours. The solution was transferred to a separating funnel and the organic layer washed with 10% aqueous ammonium chloride (2×200 mL). The organic phase was dried with anhydrous $MgSO_4$. The solvent was removed under reduced pressure to provide the bis(mesylate) as an orange oil.

Step 3. The bis(mesylate) from Step 2 was treated with a solution of NaOH (43 g, 1.075 mol) in aqueous methanol ($MeOH:H_2O=1:1$, 1.7 L). A condenser was added and the solution was refluxed for 3 hours. After cooling, the methanol was removed under reduced pressure. The resulting solution was then extracted in dichloromethane (3×300 mL). The combined organic layers were dried over anhydrous $MgSO_4$. The solvent was removed under reduced pressure and the crude product distilled at 40-60° C./0.2 Torr to provide 1,1-bis(4,4-dimethyl-1,3-oxazolin-2-yl)ethane as a colorless oil (24.6 g, 44%).

Example 2: Manganese complexation of 1,1-Bis(4,4-dimethyl-1,3-oxazolin-2-yl)ethane (Manganese complex 1)

Step 1. A solution of n-butyllithium (1.6 M in hexanes, 25 mL, 0.04 mol) was charged to a 1-L reactor vessel equipped with stirrer bar. The n-butyllithium solution was further diluted with hexane (~100 mL). A dropping funnel was charged with a solution of 1,1-bis(4,4-dimethyl-1,3-oxazolin-2-yl)ethane (9 g, 0.04 mol) in hexane (100 mL). The funnel was attached to the reactor vessel along with a paraffin bubbler to observe the release of butane gas. The ligand solution was then slowly added drop-wise to the n-butyllithium solution. Completion of the reaction was evidenced by the cessation of formation of butane gas. The solvent was removed via a trap-to-trap apparatus and the lithium salt was isolated as solid. $^1$H NMR (THF-$d_8$): δ 1.2 (s, 12H, $CMe_2$), 1.51 (s, 3H, $CH_3C(oxazolin)_2$), 3.90 (m, 4H, $OCH_2$).

Step 2. To the lithium salt from Step 1, THF (300 mL) was added to give a clear solution. $MnCl_2$ (2.5 g, 0.020 mol) was then added as a solid, and the mixture was heated at reflux for 8 hours, giving a clear solution. The mixture was cooled and the solvent was removed under reduced pressure. The residue was extracted with toluene (100 mL) and filtered by cannula. The resulting off-white solid was sublimed at 180° C./0.1 Torr to provide the manganese complex 1 as a paramagnetic solid (5 g) which could not be further characterized by NMR spectrometry.

The structure of the manganese complex 1 was tentatively assigned as shown below, possibly further including one or more solvents (THF) of crystallization which may or may not be coordinated to manganese:

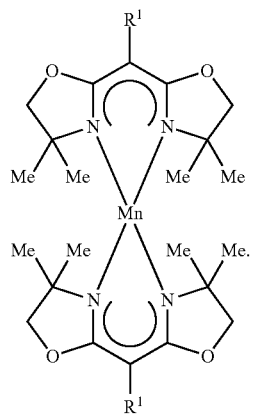

FIG. 1 shows a TGA plot of manganese complex 1 with a temperature ramp from room temperature to ~525° C.

Figure 2:
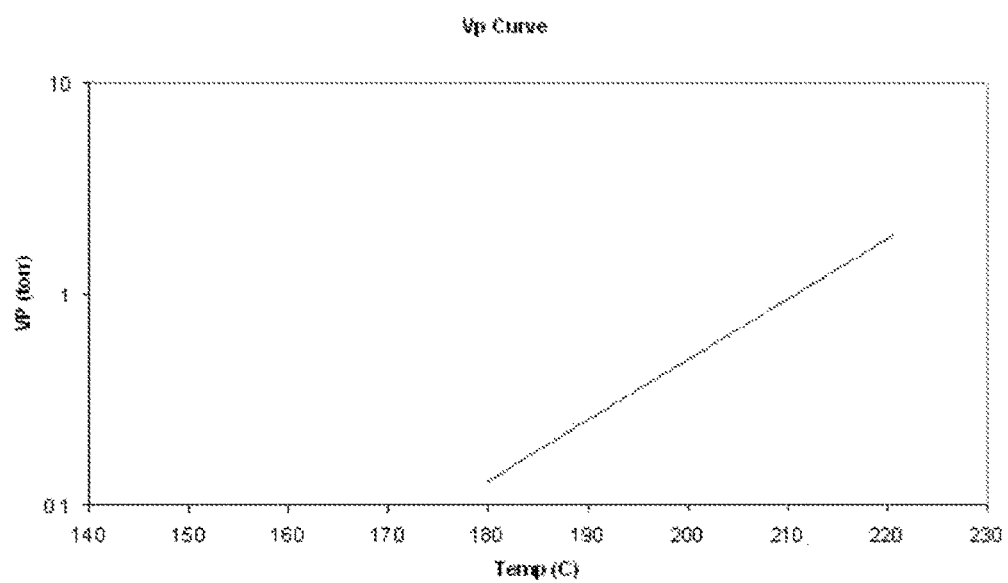
FIG. 2 is a graphical representation of vapor pressure (Torr) as a function of tempurature (° C.) for the manganese complex prepared according ti Example 2.

FIG. 2 shows vapor pressure (Torr) plotted as a function of temperature (° C.) for manganese complex 1. The vapor pressure equation for this complex was determined to be: $Log_{10}$ VP (Torr)=13.259-6415.1(1/T).

From FIGS. 1 and 2, it is readily apparent the manganese complex 1 is sufficiently volatile for use as a precursor material in an ALD or CVD process.

Example 3: CVD Studies of Maganese Complex 1

In general, conventional, pulsed CVD experiments may be carried out using a homemade tool fitted with a bubbling/vapor draw precursor inlet system. For CVD experiments targeting pure metal, nitrogen gas is employed as the carrier/purge gas.

Example 3a: CVD of with No Co-Reactant

Manganese-containing films can be deposited on substrates such as hydrogen terminated silicon, tantalum nitride, ruthenium, or thermal silicon oxide using neat manganese precursor.

CVD of the manganese precursor (160° C.) is performed using bubbler delivery. Runs are performed with a substrate temperature of 300° C. and 500 cycles with no co-reactant. Additional parameters are shown in Table 1, below.

TABLE 1

| CVD Growth Conditions with No Co-reactant | |
|---|---|
| Ampoule (precursor) temperature | 160° C. |
| Substrate temperature | 300° C. |
| Carrier gas | 0-100 sccm $N_2$ |
| Temperature of lines to chamber | 160° C. |
| Purge gas | 100 sccm $N_2$ |
| Base pressure during run | 500 mTorr |
| Pulse sequence | 2.0 sec ever 7.0 sec |

Example 3b: CVD of with N,N-Dimethylhydrazine Co-Reactant

Manganese-containing films can be deposited on substrates such as silicon with native oxide, tantalum nitride, ruthenium, or thermal silicon oxide using neat manganese precursor.

CVD of the manganese precursor is performed using vapor draw delivery. Runs are performed with a substrate temperature of 200° C. and 500 cycles with N,N-dimethylhydrazine as a co-reactant. Additional parameters are shown in Table 2.

TABLE 2

| CVD Growth Conditions with N,N-Dimethylhydrazine Co-reactant | |
| --- | --- |
| Ampoule (precursor) temperature | 160° C. |
| Substrate temperature | 200° C. |
| Carrier gas | 0-100 sccm $N_2$ |
| Temperature of lines to chamber | 160° C. |
| Purge gas | 100 sccm $N_2$ |
| Base pressure during run | 500 mTorr |
| Pulse sequence | 0.5 sec ever 20 sec |

Example 4: ALD Studies of Manganese Complex 1

In general, conventional (pulsed) ALD experiments may be carried out using a homemade tool fitted with bubbling/vapor draw precursor inlet system. For ALD experiments targeting pure metal, nitrogen gas is employed as carrier/purge gas.

Example 4a: ALD of with Hydrazine Co-Reactant

Manganese-containing films can be deposited on substrates such as hydrogen terminated silicon, tantalum nitride, ruthenium, or thermal silicon oxide using neat manganese precursor.

ALD of the manganese precursor (160° C.) is performed using bubbler delivery. Runs are performed with a substrate temperature of 200° C. and 500 cycles with hydrazine as a co-reactant. Additional parameters are shown in Table 3.

TABLE 3

| ALD Growth Conditions with Hydrazine Co-reactant | |
| --- | --- |
| Ampoule (precursor) temperature | 160° C. |
| Substrate temperature | 200° C. |
| Carrier gas | 0-100 sccm $N_2$ |
| Temperature of lines to chamber | 160° C. |
| Purge gas | 100 sccm $N_2$ |
| Base pressure during run | 500 mTorr |
| Mn precursor pulse | 2.0 sec |
| Co-reactant pulse | 1.0 sec |
| Purge between precursor pulses | 5.0 sec |

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The words "comprise", "comprises", and "comprising" are to be interpreted inclusively rather than exclusively.

What is claimed is:

1. A manganese complex of Formula I:

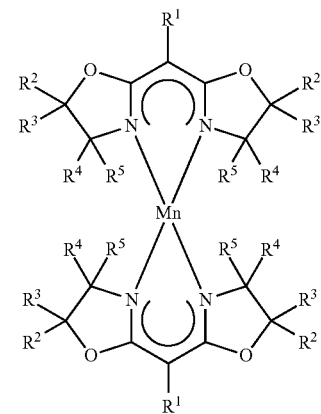

(I)

wherein
$R^1$, $R^2$, $R^3$, $R^4$, and $R^5$ are independently selected from the group consisting of hydrogen, alkyl, and trialkylsilyl.

2. The manganese complex of claim 1, wherein $R^1$, $R^2$, $R^3$, $R^4$, and $R^5$ are independently selected from the group consisting of hydrogen, $C_1$-$C_8$-alkyl, and tri($C_1$-$C_8$-alkyl)silyl.

3. The manganese complex of claim 1, wherein $R^1$, $R^2$, $R^3$, $R^4$, and $R^5$ are independently selected from the group consisting of hydrogen, methyl, ethyl, n-propyl, isopropyl, n-butyl, isobutyl, tert-butyl, n-pentyl, neopentyl, n-hexyl, n-heptyl, n-octyl, trimethylsilyl, triethylsilyl, triisopropylsilyl, and tert-butyldimethylsilyl.

4. The manganese complex of claim 1, wherein the manganese complex of Formula I is a manganese complex of Formula IA:

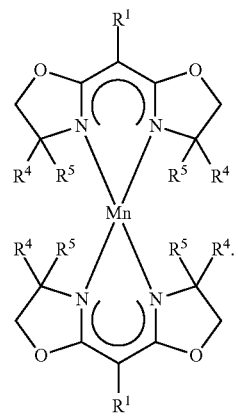

(IA)

5. The manganese complex of claim 4, wherein $R^1$, $R^4$, and $R^5$ are independently hydrogen or $C_1$-$C_8$-alkyl.

6. The manganese complex of claim 1, wherein the manganese complex is selected from the group consisting of

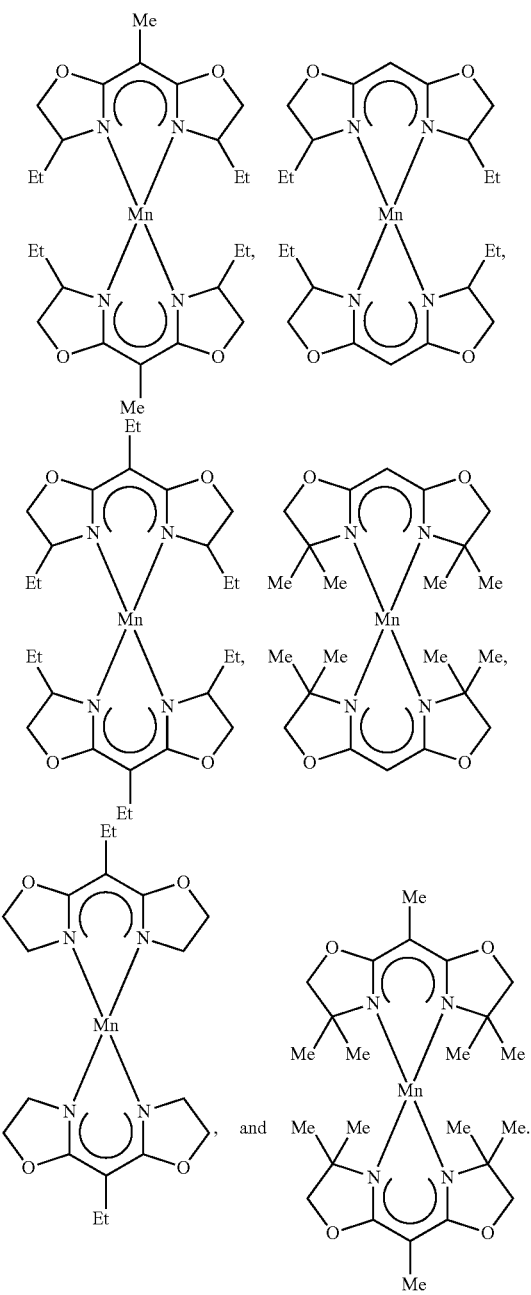

7. A method of forming a manganese-containing film by a vapor deposition process, the method comprising vaporizing the manganese complex of claim 1.

8. The method of claim 7, wherein the vapor deposition process is chemical vapor deposition.

9. The method of claim 8, wherein the chemical vapor deposition is pulsed chemical vapor deposition or continuous flow chemical vapor deposition.

10. The method of claim 9, wherein the chemical vapor deposition is liquid injection chemical vapor deposition.

11. The method of claim 7, wherein the vapor deposition process is atomic layer deposition.

12. The method of claim 11, wherein the atomic layer deposition is liquid injection atomic layer deposition or plasma-enhanced atomic layer deposition.

13. The method of claim 7, wherein the manganese complex is delivered to a substrate in pulses alternating with pulses of an oxygen source.

14. The method of claim 13, wherein the oxygen source is selected from the group consisting of $H_2O$, $H_2O_2$, $O_2$, ozone, air, i-PrOH, t-BuOH, and $N_2O$.

15. The method of claim 7, further comprising vaporizing at least one co-reactant selected from the group consisting of hydrogen, hydrogen plasma, oxygen, air, water, ammonia, a hydrazine, a borane, a silane, ozone, and a combination of any two or more thereof.

16. The method of claim 15, wherein the at least one co-reactant is a hydrazine.

17. The method of claim 16, wherein the hydrazine is hydrazine ($N_2H_4$) or N,N-dimethylhydrazine.

18. The method of claim 7, wherein the method is used for a DRAM or CMOS application.

19. A method of making a manganese complex of Formula I, the method comprising:
reacting a compound of Formula II:

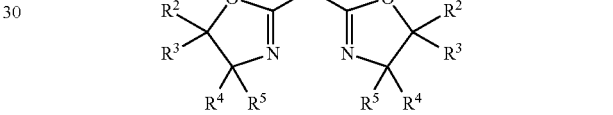

or the conjugate base thereof,
with a manganese salt to provide the manganese complex of Formula I:

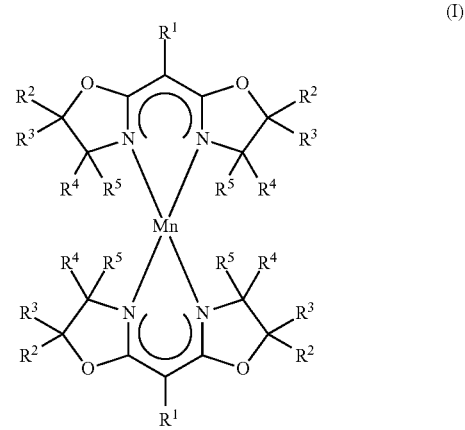

wherein
$R^1$, $R^2$, $R^3$, $R^4$, and $R^5$ are independently selected from the group consisting of hydrogen, alkyl, and trialkylsilyl.

* * * * *